US00PP08672P

United States Patent [19]

Winchel

[11] Patent Number: Plant 8,672

[45] Date of Patent: Apr. 5, 1994

[54] HYBRID TEA ROSE PLANT NAMED EDITOR TOMMY CAIRNS

[75] Inventor: Joseph F. Winchel, Harbor City, Calif.

[73] Assignee: Coiner Nursery, La Verne, Calif.

[21] Appl. No.: 787,418

[22] Filed: Nov. 4, 1991

[51] Int. Cl.[5] ..... A01H 5/00

[52] U.S. Cl. ..... Plt./11

[58] Field of Search ..... Plt. 11, 12, 19

*Primary Examiner*—Howard J. Locker

*Attorney, Agent, or Firm*—Coiner Nursery

[57] ABSTRACT

A new rose variety of the hybrid tea class characterized by having deep pink blooms with paler reverse, on a tall growing bush with deep green foliage.

1 Drawing Sheet

The present invention relates to a new and distinctive variety of rose plant of the hybrid tea class, which was originated by crossing two unnamed seedlings and first observed in Spring, 1987.

Among the novel characteristics possessed by the new variety which distinguish it from its parents and all other varieties of which I am aware of are:

(1) A deep pink bloom with paler reverse;
(2) A vigorous upright plant;
(3) Exhibition form bloom;
(4) Disease resistant; and
(5) Free bloomer.

Asexual reproduction of the new rose variety by budding, as performed at Wasco, Calif. shows that the aforementioned characteristics and distinctions come true to form and are established and transmitted through succeeding propagations.

The accompanying drawing shows typical specimens of the vegetative growth and flowers of the new variety in different stages of development and as depicted in color as nearly true as it is reasonably possible to make in a color illustration of this character.

The following is a detailed description of the new variety, with color terminology in accordance with the *PANTONE Color Formula Guide 747XR*. The terminology used in the color description herein refers to plate numbers in the aforementioned color chart, e.g. "PANTONE 182U" is plate "PANTONE 182U" of the *PANTONE Color Guide 747XR*. The use of the letters "C" and "U" after the plate numbers refers to the stock on which the ink is applied. "C" designates coated stock and "U" designates uncoated stock.

American Rose Society Registration commercial appellation:

"Editor Tommy Cairns"

IRAR Appellation: "Editor Tommy Cairns".
Parentage: Seedling.
*Cross.*—Two unnamed seedlings.
Class: Hybrid Tea.

The following observations are made of specimens grown outdoors in Kern County, Calif., in the month of November.

FLOWER

Blooming Habit

A. Bud:
(1) *Size.*—Medium.
(2) *Form.*—Pointed with high center.
(3) *Sepals.*—Usually 3-5 cm with normal extension. Slight serration with no consistant number of appendages. Color, close to PANTONE 576U.
(4) *Peduncle.*—9-10 cm, very strong and erect. Color close to PANTONE 582U, smooth surface.
(5) *Color when sepals first divide.*—Close to PANTONE Basic Colors 1 XR PANTONE Rhodamine Red U. Bud — green close to PANTONE 582U.

B. Bloom:
(1) *Size.*—About 11.5 cm in diameter. Usual depth of bloom is 5.5 cm. Petals are wider than long averaging 2.5 cm×2 cm.
(2) *Borne.*—One to the stem.
(3) *Form.*—Full and high-centered at first — with petals tightly rolled outward, becoming open and high-centered at maturity.
(4) *Petalage.*—Usually around 40.
(5) *Color.*—Deep pink, close to PANTONE 232U, with a paler underside close to PANTONE 230U fading to white.

C. Petals:
(1) *Texture.*—Velvety.
(2) *Form.*—Ovoid.
(3) *Arrangement.*—Regular at all stages — loose with aging.
(4) *Petaloids.*—None.
(5) *Fragrance.*—Medium.
(6) *Lasting quality.*—Planted outside in Southern California averages 6 to 14 days depending on climate. As a cut flower the lasting quality averages 7 days.

REPRODUCTIVE ORGANS

A. Stamen:
(1) *Arrangement.*—Around pistil.
(2) *Number.*—Average, close to 100.
(3) *Length.*—Average 1.5 cm.
(4) *Filament.*—About 1.25 cm and close to PANTONE 129U.
(5) *Anthers.*—0.07 cm, color PANTONE 177U fading to PANTONE 176U.

(6) *Pollen.*—Normal amount, yellow.

B. Pistil:

(1) *Styles.*—Average 1 mm, color close to PANTONE 139C to PANTONE 129U, number averages 150.

(2) *Stigma.*—Color close to PANTONE 129U.

(3) *Ovary.*—Round.

(4) Average height.—1.5 cm.

C. Hips: Will accept pollen.

(1) *Shape.*—Round.

(2) *Color.*—Orange when ripe, color close to PANTONE 1385U.

(3) *Seeds.* 10–15.

PLANT

A. Form: Upright, averaging over 4 feet in California climate. Strong stems averaging 4 feet–6 feet from bud union to bloom.

B. Growth: Vigorous.

C. Foliage:

(1) *Size.*—Medium.

(2) *Quantity.*—Average, 5 to 7 leaflets.

(3) *Color.*—New foliage, red — color close to PANTONE 378C. Mature foliage, deep green — color close to PANTONE 5743C.

(4) *Shape.*—Oval with pointed center.

(5) *Texture.*—Glossy.

(6) *Edge.*—Serrated.

D. Wood:

(1) *New wood.*—Color close to PANTONE 497C.

(2) *Mature wood.*—Color close to PANTONE 378C.

E. Thorns:

(1) *Color.*—New, immature color close to PANTONE 584U. Mature thorn color close to PANTONE 4635C.

(2) *Length.*—Average 1 cm, hooking downward. An average of 25 thorns are on a 10 cm length of mature stem.

F. Resistance to disease:

(1) *Mildew.*—Good.

(2) *Rust.*—Good.

(3) *Black spot.*—Good.

G. Winter hardiness: Average.

I claim:

1. A new and distinctive variety of rose plant of the hybrid tea class, substantially as herein shown and described.

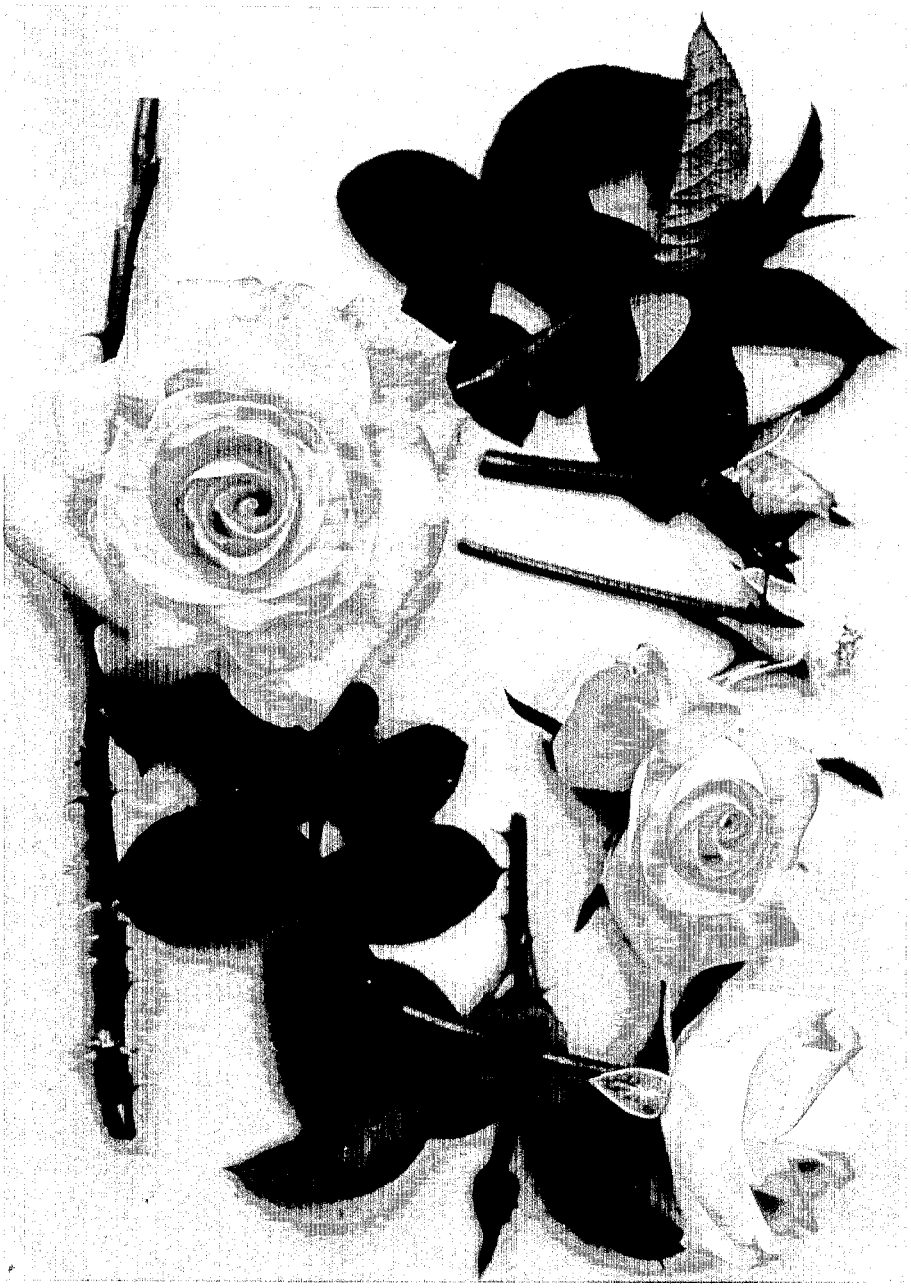

* * * * *